United States Patent
Wu et al.

(10) Patent No.: US 9,592,257 B2
(45) Date of Patent: Mar. 14, 2017

(54) COMPLETE HUMAN SKIN ORGAN GENERATED FROM CULTURE-EXPANDED CELLS

(71) Applicant: MWV Cell, LLC, Atlanta, GA (US)

(72) Inventors: Xunwei Wu, Medford, MA (US); Bryan T. Marshall, Atlanta, GA (US); Minh Vo, Sugar Hill, GA (US)

( * ) Notice: Subject to any disclaimer, the term of this patent is extended or adjusted under 35 U.S.C. 154(b) by 0 days.

(21) Appl. No.: 14/514,364

(22) Filed: Oct. 14, 2014

(65) Prior Publication Data

US 2015/0104432 A1    Apr. 16, 2015

Related U.S. Application Data

(60) Provisional application No. 61/890,145, filed on Oct. 11, 2013.

(51) Int. Cl.
| | |
|---|---|
| *C12N 5/071* | (2010.01) |
| *C12N 5/077* | (2010.01) |
| *A61K 35/36* | (2015.01) |
| *A61F 2/10* | (2006.01) |

(52) U.S. Cl.
CPC ............ *A61K 35/36* (2013.01); *C12N 5/0698* (2013.01)

(58) Field of Classification Search
None
See application file for complete search history.

(56) References Cited

U.S. PATENT DOCUMENTS

| | | | | |
|---|---|---|---|---|
| 2002/0028192 | A1* | 3/2002 | Dimitrijevich | A61L 27/24 424/93.7 |
| 2011/0243903 | A1* | 10/2011 | McBride | C12N 5/0629 424/93.7 |
| 2011/0321180 | A1* | 12/2011 | Lee | C12N 5/0628 800/9 |

OTHER PUBLICATIONS

Li et al, Nature Communications, Mar. 2011, vol. 2, pp. 1-8.*
NIH Stem Cell Information: Glossary. Obtained from http://stemcells.nih.gov/info/pages/glossary.aspx on Mar. 7, 2016, 4 pages.*

* cited by examiner

*Primary Examiner* — Allison Fox
(74) *Attorney, Agent, or Firm* — Long Technology Law, LLC; Jospeh L. Long (57) ABSTRACT

Systems and methods can support generation of a full-thickness, human skin organ from tissue culture expanded cells. Human dermal and epidermal progenitor cells can be isolated from human tissues. Isolated cells may be cultured as epidermal cells while other isolated cells may be separately cultured as dermal cells. The cultured epidermal cells and dermal cells may be combined for co-culturing. The co-cultured cells may be suspended within a slurry. The co-cultured cells may be implanted onto a recipient organism for generation of a full-thickness skin organ comprising fully cycling hair follicles, adipose tissue, and other skin organ structures.

20 Claims, 4 Drawing Sheets

COMPLETE HUMAN SKIN ORGAN GENERATED FROM CULTURE-EXPANDED CELLS

RELATED APPLICATION

This application claims priority to U.S. Provisional Patent Application No. 61/890,145, filed Oct. 11, 2013 and entitled "Generating a Complete Human Skin Organ with Culture-Expanded Cells." The complete disclosure of the above-identified priority application is hereby fully incorporated herein by reference.

BACKGROUND

A goal of regenerative medicine is to produce a fully functional tissue or organ to replace one that has been damaged or destroyed by injury, disease, or aging. Currently, treatment of a full-thickness skin wound such as a deep burn or chronic ulcer represents a significant clinical challenge. Autologous skin grafts are considered to be the best treatment for such wounds but have multiple drawbacks and limitations. For instance, if the defect area exceeds fifty percent of total body surface area, it is often not practical to use autologous skin grafting due to shortage of donor sites. Furthermore, an additional wound is created at the donor site. Traditional skin grafts, once healed, can provide a barrier function, but generally do not contain sweat glands, hair follicles, or fully developed sub-cutis.

To address the limitation of donor sites, tissue-engineered skin has been developed using in vitro cultured cells. Such skin equivalents, or skin substitutes, have been used to repair cutaneous wounds due to trauma, burn, surgery, or chronic ulceration. The application of skin substitute as an alternative to autologous skin grafts has had limited long-term clinical success because substitutes lack neither normal dermal structure. The substitutes also lack the structures critical for normal functioning skin such as sweat glands, hair follicles, and sub-cutis.

There is a need in the art for a method to culture human cells while retaining and enhancing their ability to completely regenerate a full-thickness human skin organ that can interact with other cells and form functioning skin structures such as sweat glands, nerves, hair follicles, blood vessel, and adipose. There are unmet clinical needs for therapies to treat deep wounds, burns, chronic wounds, and so forth while avoiding scarring.

SUMMARY

In certain example embodiments described herein, methods and systems can support generation of a full-thickness, human skin organ from tissue culture expanded cells. Human dermal and epidermal progenitor cells can be isolated from human tissues. Isolated cells may be cultured as epidermal cells while other isolated cells may be separately cultured as dermal cells. The cultured epidermal cells and dermal cells may be combined for co-culturing. The co-cultured cells may be suspended within a slurry. The co-cultured cells may be implanted onto a recipient organism for generation of a full-thickness skin organ comprising fully cycling hair follicles, adipose tissue, and other skin organ structures.

These and other aspects, objects, features, and advantages of the example embodiments will become apparent to those having ordinary skill in the art upon consideration of the following detailed description of illustrated example embodiments.

DETAILED DESCRIPTION OF EXAMPLE EMBODIMENTS

Overview

The methods and systems described herein enable tissue engineering and regenerative techniques to reconstitute human skin organs. Human dermal and epidermal progenitor cells can be isolated, tissue culture expanded, cryopreserved, and grafted to produce a complete human skin organ. The complete human organ produced can be a full-thickness skin with human sweat glands, sebaceous glands, nerves, muscle, blood vessels, epidermis, dermis, sub-cutis, adipose, and hair follicles. The generated skin organ can heal itself as typical human skin does. Hair follicles associated with the generated skin organ can cycle as normal and demonstrate formation of stem cell niches within the organ.

Cells may be sourced and isolated from human tissue. Preferably, these cells may be SOX2 positive. SOX2 is a gene that encodes transcription factors regulating embryonic development and determining cell fate. For example, SOX2 is integral in stem-cell maintenance within the central nervous system. According to certain embodiments, SOX2 positive cell populations may be sourced from fetal scalp tissue, adult scalp tissue, neonatal foreskin tissue, other human tissues, or any combination thereof.

An in vitro culture medium presented herein can maintain multipotent and trichogenic qualities of the isolated human epidermal and dermal cells. Furthermore, trichogenicity of collected skin cells may be enhanced by aggregation culture or low-oxygen culture. The combination of epidermal and dermal cells after separate culturing may be placed on a substrate such as a membrane. The membrane with the adherent cells may then be placed on a skin wound. The techniques presented for culture-expansion and implantation of these cells can support in situ production of full-thickness human skin comprising structures critical for normal functioning skin such as sweat glands, hair follicles, and sub-cutis. Sweat glands can support temperature control. Hair follicles can regulate temperature and are cosmetically desirable. In addition, hair follicles provide a reservoir of both dermal and epidermal stem cells. The sub-cutis provides insulation and signaling molecules, which interact with the dermis to control the mechanical properties of skin.

The functionality of the various example embodiments will be explained in more detail in the following description, read in conjunction with the figures illustrating the program flow. Turning now to the drawings, in which like numerals indicate like (but not necessarily identical) elements throughout the figures, example embodiments are described in detail.

Example Structures

Figure 1:
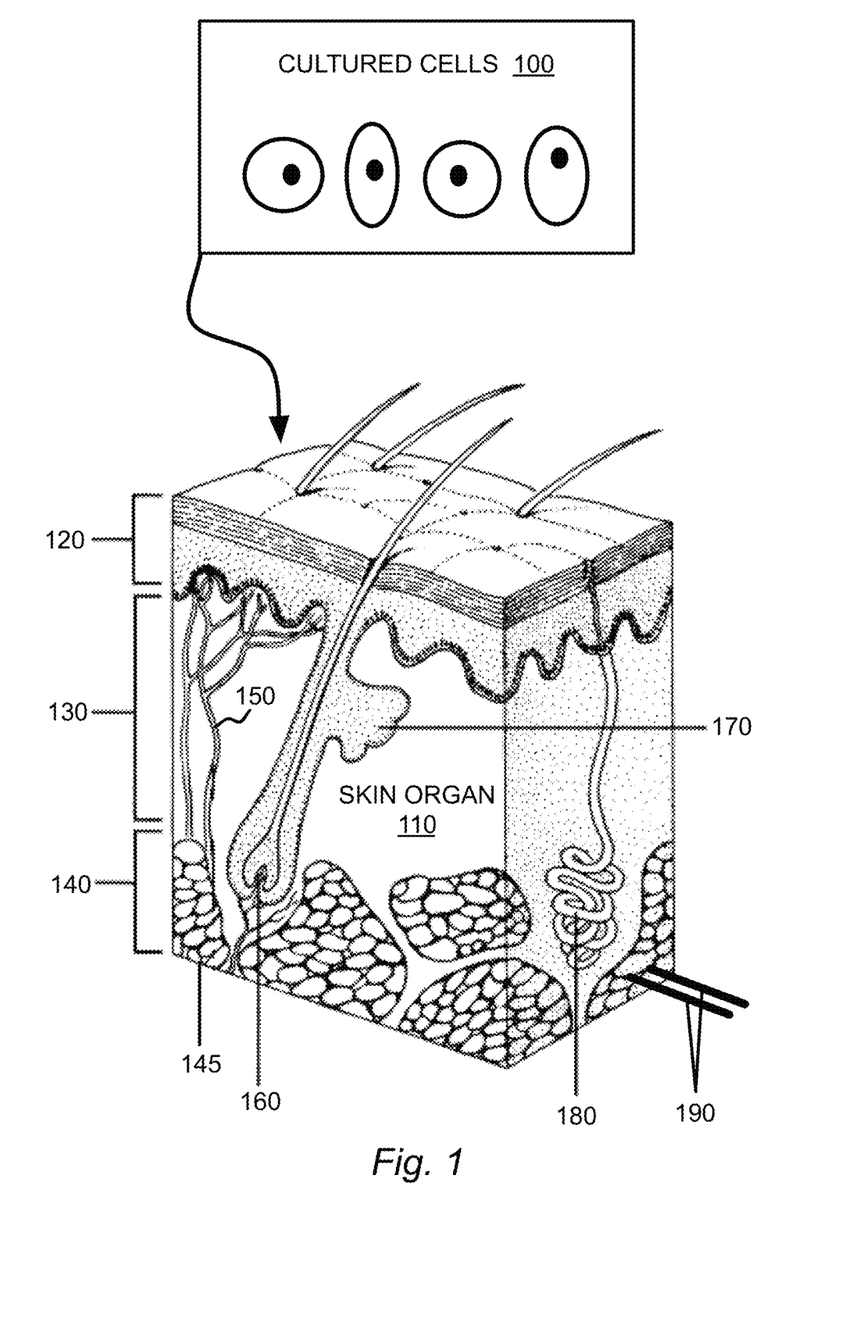
FIG. 1 is a schematic diagram illustrating cultured cells generating a full-thickness, functional skin organ in accordance with one or more embodiments presented herein.

FIG. 1 is a schematic diagram illustrating cultured cells 100 generating a full-thickness, functional skin organ 110 in accordance with one or more embodiments presented herein. The skin organ 110 may be generated to include all three layers of epidermis 120, dermis 130, and subcutis 140. The subcutis 140 may also be referred to as the hypodermis. The skin organ 110 may also be generated to include the functional structures of skin such as adipose tissue 145, nerves 150, hair follicles 160, sebaceous glands 170, sweat glands 180, and blood vessels 190.

Production of the cultured cells 100 can begin by sourcing and isolating epidermal cells and dermal cells from human tissues. For example, the cells may be isolated from fetal scalp tissue, adult scalp tissues, or neonatal foreskin tissues. The isolated cells can be enriched and maintained as a mulitpotent, SOX2-positive population of cells. The isolation methods and the cell culture methods may both select for multipotent cells. The dermal and epidermal cell types may be separately cultured in a specific medium for multiple passage cycles. For each passage, the cells may be sub-cultured or split and grown under cultured conditions for extended periods of time to increase the number of cells. Each cycle where the cells are transferred from one vessel to another may be considered a passage cycle. Cell cultures established under low oxygen conditions (two to ten percent oxygen) can increase SOX2 expression. Aggregation cultures can maintain multipotent populations of both dermal and epidermal cells. A method of cryopreservation may be used to establish a bank of multipotent cells.

The combination of dissociated, culture-expanded human dermal and epidermal cells may be attached to a slightly permeable silicone membrane for grafting. The reconstituted skin organ 110 can contain an intact epidermis 120 with normal pigmentation, dermis 130, mature cycling hair follicles 160, blood vessels 190, nerves 150, sebaceous glands 170, eccrine sweat glands 180, and a subcutis including adipose tissue. The reconstituted skin organ 110 may cover an area of up to two square centimeters.

The reconstituted skin organ 110 may include 50-2000 mature hair follicles 160 square centimeters. The hair follicles 160 may be tubular mammalian skin structures that produce hair. A normal hair follicle 160 can contain a hair shaft filament growing from the deep follicle. The regenerated hair follicles 160 can have normally layered sheaths with sebaceous glands, arrector pili muscles, dermal papilla, and mature hair shafts. The hair follicles 160 can show normal hair follicle cycling. One phase of cycling is the anagen phase, or active growth phase, of the hair follicle 160 during which the hair shaft is growing. The hair follicles 160 can also show catagen phase, or transition phase, that occur at the end of the anagen phase signaling the end of the active growth of a hair. The hair follicles 160 can also show telogen phase, or resting phase, of the hair follicle 160 during which hair growth is absent.

It should be appreciated that dermal cells or dermal fibroblasts may include cells that surround and interact with the hair follicle 160. These cells have inherent follicle-inducing activity. Other dermal cells make up the dermis 130, or second layer of skin, which are responsible for generating the connective tissue that unites separate cell layers and allows the skin to recover from injury. In contrast, epidermal cells can provide the epidermis 120 or outermost layer of the skin. The epidermis 120 may be composed primarily of keratinocytes. The epidermis 120 may also include the epithelial cells that make up the hair follicle 160. Melanocytes, or melanin-producing cells, are responsible for skin pigmentation and may be located within the bottom layer of the epidermis 120 and in the bottom of the hair follicle 160. The subcutis 140 can provide the deepest layer of the skin organ 110. The subcutis 140 can join to the bottom of the dermis 130.

It should be appreciated that skin appendages can include various structures associated with the skin including, but not limited to, hairs, sweat glands 180, and sebaceous glands 170. The pilosebaceous unit can include a hair follicle 160 and its associated sebaceous gland 170. The sebaceous glands 170 may grow out from the upper hair follicle 160. The sebaceous glands 170 may secrete an oily/waxy matter called sebum into the canal of the hair follicle 160. Sebum can lubricate and waterproof the skin and hair. Dermal papilla cells can form a small, nipple-like structure at the base of the hair follicle 160. The dermal sheath, a connective tissue, can line the hair follicle 160.

Figure 2:
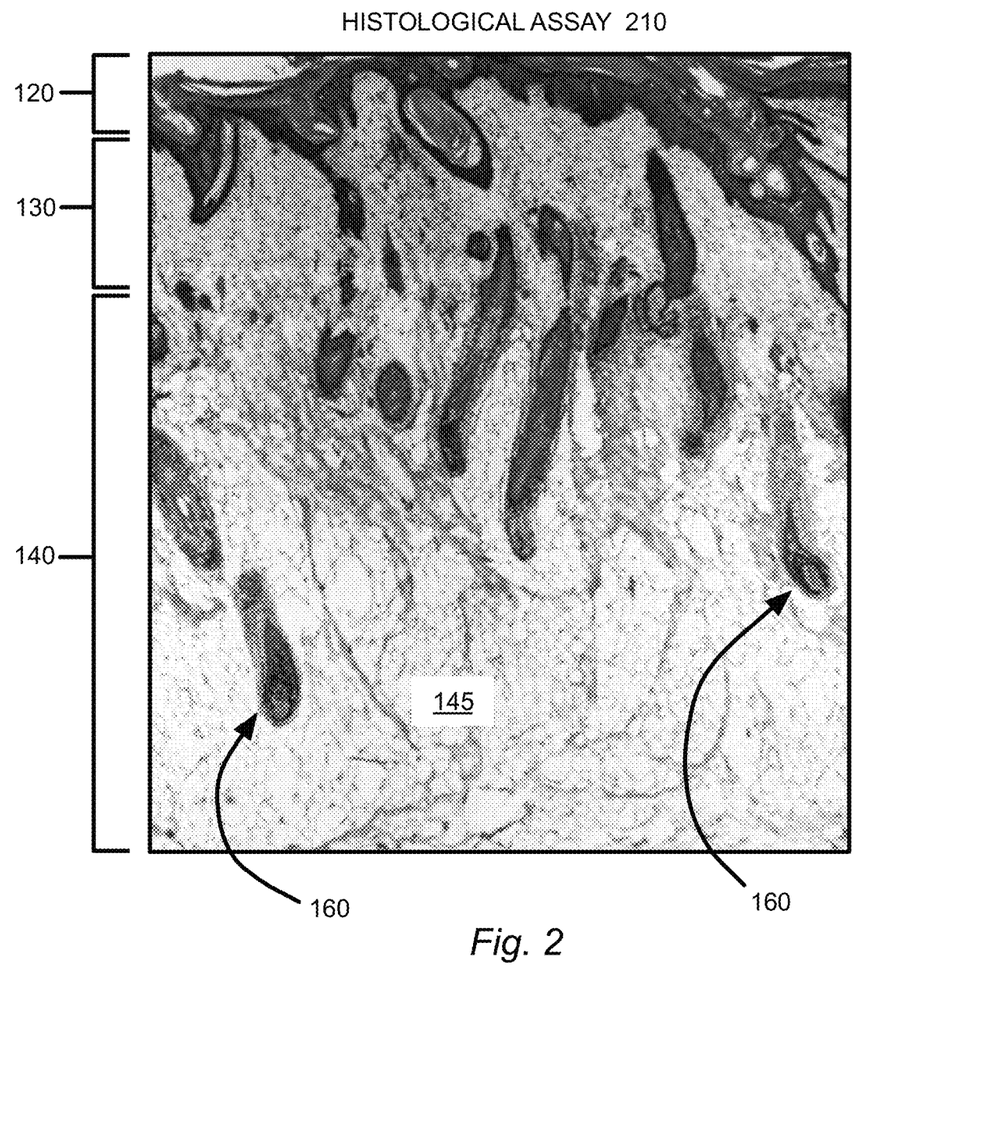
FIG. 2 illustrates a histological assay of a human skin organ grown on a mouse in accordance with one or more embodiments presented herein.

FIG. 2 illustrates a histological assay 210 of a human skin organ 110 grown on a mouse in accordance with one or more embodiments presented herein. The stained histological assay 210 shows full-thickness skin organ 110 including epidermis 120, dermis 130, and subcutis 140. The subcutis 140 supports adipose tissue 145 and the skin organ 110 includes skin appendages such as hair follicles 160. The skin organ 110 shown in the histological assay 210 was grown from a graft of human cells onto an immunodeficient mouse to prevent rejection of the graft.

To prepare the cell culture in this example, dissociated epidermal cells were derived from human fetal scalp, human adult scalp, and human newborn foreskin. Dermal cells were derived from human fetal scalp and adult scalp. After isolation of the cells from tissues, primary cultures containing dermal cells were maintained in culture. Primary cultures of epidermal cells were maintained in commercial medium plus Rho-associated protein kinase (ROCK) inhibitor, Y27632. Both dermal and epidermal cells were propagated separately up to the sixth passes for up to three weeks, and were then mixed in a one-to-one ratio to produce a cell slurry. The cell slurry was subsequently transferred onto a silicon membrane and incubated at 37 degrees Celsius for approximately an hour in a cell culture incubator to allow the cells to adhere to the membrane.

To prepare for the graft, full-thickness skin was removed from the back of a immunodeficient mouse to make a wound. The silicon membrane with adherent cells was placed onto the undamaged musculature fascial plane at the base of the surgical wound with cells contacting the wound and the silicon membrane on top. The membrane was subsequently sutured to the host skin. A sterile dressing with ointment was applied over the wound and the mouse were wrapped with sterile tape and monitored over the course of the following 12-14 weeks.

The skin organ 110 generated on the mouse and the associated hair follicles 160 (including interfolliclular epidermis, follicular epidermis, dermal fibroblasts, dermal papilla, and dermal sheath) are of human origin. Staining for differentiation markers documented good follicular and interfollicular epidermal maturation. The regenerated interfollicular and follicular epidermis showed distinct differentiated layers. The reconstituted skin established its own stem cell niches, maintained human features for at least a year after grafting, and was able to heal with human cells after injury.

The regenerated tissue was examined by dissecting light microscopy and then sectioned for high magnification light microscopy using hematoxylin and eosin stains. Staining was carried out according to standard protocol and then examined by light microscopy.

After the graft surgery, pigmented skin formed in four weeks. At twelve weeks, pigmented hair shafts emerging from the skin surface were clearly visible by eye and continued to grow until fourteen weeks post-graft. Robust pigmented hairs were clearly visible in the grafted area. The fact that the hairs were pigmented is a direct indication that the epidermal cell culture contains melanocytes and that the reconstituted hair follicles 160 resulted from the grafted human cells. The mouse used for the graft does not produce pigmented hair.

Hair follicles 160 in the reconstituted skin have mature shafts associated with sebaceous glands 170 and dermal papillae. The hair follicles 160 are able to cycle. Individual hair follicles 160 were isolated under a dissection microscope. The regenerated hair follicles exhibit mature features, namely, different layers including a pigmented hair shaft, an inner root sheath, and an outer root sheath. The hair follicle 160 was associated with sebaceous glands 170 and dermal papillae. Follicles in the anagen phase with a strongly pigmented shaft bulb area attached to a cupped dermal papilla were observed, as well as telogen-like follicles with much less pigmented shafts and dermal papillae which are located at the tip of the hair follicle 160. The presence of both anagen and telogen follicles in the same graft indicates that the regenerated hair follicles 160 are cycling. The ability of hair follicles 160 to cycle is an important criterion defining a mature hair follicle 160. Hairs were trimmed short to allow hair cycle phases to be observed. Regrowth of hairs one month after trimming was observed.

Formation of mature dermal papillae in the reconstituted hair follicles 160 was monitored using alkaline phosphatase staining Alkaline phosphatase is a marker distinguishing dermal papillae from other dermal fibroblasts. To further characterize the regenerated hairs and skin, alkaline phosphatase staining was carried out on six-week and twelve-week old grafts. Papillae with alkaline phosphatase positive blue staining were located at the proximal tip of early stage (stage three) hair follicles of six-week old grafts, and were cupped by a mature anagen hair follicle of the twelve-week old grafts. Taken together, these data indicate that the reconstituted hair follicles have mature shafts associated with sebaceous glands 170 and mature dermal papillae.

Green colored hair follicles 160 were reconstituted from cultured green fluorescent protein (GFP)-expressing cells. To demonstrate that the regenerated hair follicles were formed from grafted cells, cultured foreskin keratinocytes were infected with a GFP-expressing retrovirus vector prior to grafting, allowing the grafted cells to be traced by fluorescence microscopy. Twelve weeks after grafting, thin layers of skin were dissected from the graft and were analyzed by fluorescence microscopy. Mature hair follicles 160 associated with sebaceous glands 170 could be seen from the phase contrast image. All epidermal parts, including follicles, sebaceous glands, and the interfollicular epidermis were fluorescent green, indicating that they originated from GFP-expressing keratinocytes. By contrast, all dermal parts including papillae were negative for GFP.

In addition, fetal scalp dermal cells infected with GFP-expressing retrovirus were combined with wild-type epidermal cells and grafted onto mice. Twelve weeks later, the grafted tissue was harvested and analyzed for GFP expression under a fluorescent microscope. All dermal portions were positive for GFP (including the dermal papilla), while all the epidermal areas of the graft were negative for GFP. These data strongly support the conclusion that the reconstituted skin and hair follicles formed from the implanted dissociated cultured human epidermal and dermal cells.

This result showed the genetic manipulation of cells in vitro would not affect the formation of reconstituted hair producing skin. It suggests specific human skin or disease model can be reconstituted by this system.

Human specific antibodies were analyzed by immunofluorescence microscopy to reconfirm that the generated skin (dermis, epidermis, sub-cutis, blood vessels, nerve, muscles, sweat glands, sebaceous glands, and hair follicles) are human in origin. The expression of two human-specific markers in mouse grafts indicated that the regenerated hair follicles 160 and epidermis 120 harvested from the mice are derived from human cells.

In order to test the reconstituted human skin organ 110 is a functional skin, ulcer wounds were created in the center of the regenerated skins using a biopsy punch. At day seven after injury, the control wound on the host mouse skin had completely reepithelialized. By contrast, at the same time, the regenerated skin showed only an epithelial tongue extending into the wound but with incomplete closure. By fourteen days, the wound in the reconstituted skin was completely reepithelialized. The healing process in the regenerated human skin is very similar to that reported on transplanting the human full-thickness skin onto mice. It was tested if the reparative cells were human or mouse. Using human specific pan-cytokeratin antibody, it was found that host mouse skin epidermis did not stain but the epithelial tongue (at day seven) and the fully covered wound (at day fourteen) were positive. This indicated that the reparative epithelial cells were human. When human specific vimentin antibody was used to test the origin of the cells repairing the dermis, it was also found that the adjacent mouse skin was negative and the reparataive dermis showed infiltration of cells expressing human vimentin. This study showed the reconstituted skin has reparative properties, suggesting it is a functional skin.

SOX2 is expressed in skin derived dermal cells in vitro and highly expressed in dermal papilla and dermal sheath cells in vivo. Using real time RT-PCR analysis, it was found that SOX2 was significantly up-regulated in skin derived dermal cells compared to the level of both mesenchymal stem cells (MSCs) and foreskin-derived fibroblasts. The role of SOX2 was probed in human follicular development using immunofluorescence on human fetal scalp skin specimens. SOX2 expression appears during the initial aggregation of cells that form the dermal condensate and is present throughout the morphogenic process. The expression of SOX2 in the adult scalp was also investigated. Using immunofluorescence, SOX2 protein expression was identified in the dermal papilla, dermal sheath, and dermal sheath cup of adult scalp hair follicles. These studies demonstrate that SOX2 plays a role in both hair follicle morphogenesis and maintenance.

Higher SOX2 expressed cells may be more trichogenic when enhanced by aggregation culture. The SOX2 expression in the cultured human cells and in two follicular neogenesis assays was examined. SOX2 was present both in the cultured cells and in the dermal portion of the follicles formed in the neogenesis assays. In aggregate, these results indicate that the cells of the dermal papilla and sheath express SOX2 in the human scalp. When isolated and cultured, these cells continue to express SOX2 and that these cultured SOX2 cells can induce hair follicle formation in follicle neogenesis assays.

The apparent relationship between SOX2 and trichogenicity prompted the development of culture conditions to enhance SOX2 expression presented herein. Two culture methods were developed which enhanced the expression of SOX2 in cultured cells. In the first method, SKP culture conditions select for a sphere forming subpopulation. In a paired study, the SOX2 content and trichogenicity of monolayer culture to the sphere forming subpopulation was compared. The cells within the sphere forming population expressed a significantly higher level of SOX2 and were more trichogenic.

In the second culture method, a modified low-oxygen environmental condition was evaluated for changes in SOX2 expression and trichogenicity. In a paired study, cells cultured under normal environmental conditions were compared to cells cultured in the low oxygen condition. The modified low-oxygen environment significantly increased SOX2 expression and trichogenicity.

It can be concluded from these results that regenerated human skin complete organ can be successfully regenerated by grafting dissociated and cultured fetal scalp epidermal cells or foreskin keratinocytes. Furthermore, the regenerated human hair follicles 160 are capable of forming mature hair shafts associated with sebaceous glands 170 and dermal papillae.

The animals generated in this example may be useful in the study of human disease and for screening of compounds for treatment of normal or diseased skin or hair. The skin used to provide the cells may be obtained from a human with a disease to be studied, or for which a compound is to be screened for an effect. In this method for making full thickness human skin on the back of an immunoincompetent animal using normal human skin, a suspension of a mixture of cultured and passaged human multipotent and differentiated dermal and epidermal cells is prepared, adhered to an inert biocompatible substrate suitable for application to wounds in skin, wounds at a site where skin is desired are made on the animal, and the cell-substrate is applied, cell side to the wound. Once the skin and/or hair follicles have formed, compounds to be tested can be applied to the skin and compared to untreated skin, or areas formed from diseased skin cells can be compared to areas formed from normal skin cells.

The reconstituted skin includes three main layers: epidermis 120, dermis 130, and subcutis 140. The epidermis 120 is composed mostly of keratinocytes. Penetrating the epidermis 120 are sweat glands and hair shafts. The epidermis 120 sits on the dermis 130 while the dermis 130 sits on the subcutis 140. The subcutis 140 is the deepest layer of the skin and contains lipocytes, which produce lipids for the subcutaneous tissue to make a layer of adipose tissue 145 that can cushion muscles, bones and inner organs. The adipose tissue 145 can act as an insulator and an energy reservoir. Nerves and blood vessels are created throughout the organ and arector pili muscles and sebaceous glands are associated with the hair follicles 160.

The hair shaft of the reconstituted skin can generally extend from the dermis 130 out onto the epidermis 120. The dermal part of the hair follicle 160 has two main parts: the dermal papilla and the dermal sheath. By definition, mature hair follicles 160 have dermal papillae at the base or bulb, proliferating cells positioned proximally, and differentiating cells positioned distally, thereby facilitating a proximal-distal growth mode. The hair follicle 160 is composed of concentric layers of outer and inner root sheath, cuticle, cortex and medulla. The shaft, which is the product of the follicle, has a unique molecular constitution. The follicle is also associated with sebaceous glands 170, and has the ability to regenerate a new hair organ through repeated cycles of growth (anagen), regression (catagen), and quiescence (telogen).

Example Processes

According to methods and blocks described in the embodiments presented herein, and, in alternative embodiments, certain blocks can be performed in a different order, in parallel with one another, omitted entirely, and/or combined between different example methods, and/or certain additional blocks can be performed, without departing from the scope and spirit of the invention. Accordingly, such alternative embodiments are included in the invention described herein.

Figure 3:
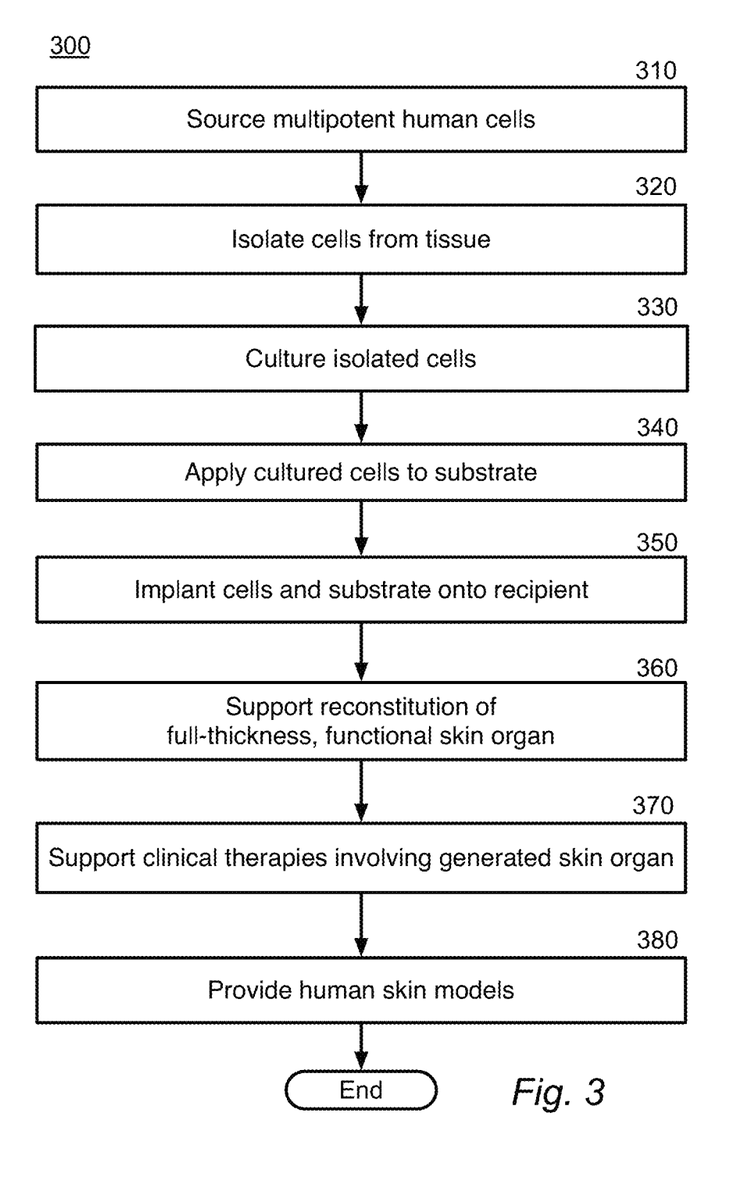
FIG. 3 is a block flow diagram depicting a method for generating a full-thickness, human skin organ from cultured cells in accordance with one or more embodiments presented herein.

FIG. 3 is a block flow diagram depicting a method 300 for generating a full-thickness, human skin organ 110 from cultured cells 100 in accordance with one or more embodiments presented herein.

In block 310, multipotent human cells may be sourced. The skin progenitor cells may be human dermal and epidermal cells. Dermal progenitor cells may be isolated from the follicular portion of human skin. The isolated cells may comprise pluripotent follicle-derived cells. A portion of the cells may be SOX2 positive. SOX2 expressed dermal cells may be highly trichogenic. SOX2-expressed cells may be sourced from the dermal papilla and the sheath of adult human scalp follicles. The expanded cells can be multipotent multipotent and trichogenic. SOX2 expression may be maintained and enriched by aggregation in vitro culture. It should be appreciated that these cell sources may initially be tissues. In practice, when referring to a cell or cells, these methods may apply to aggregates of cells or even tissues.

Hair follicles can provide a reservoir of both dermal and epidermal stem cells. Epithelial stem cell markers have been identified in the outer root sheath bulge region of the hair follicle. Cell markers can identify the dermal papilla, a reservoir of stem cells that has been differentiated along adipogenic, osteogenic, and neural lineages. Autologous sourced cells or tissues may be obtained from the same individual such that the donor and recipient are one and the same. Allogeneic sources may be genetically different although belonging to, or obtained from, the same species.

Dissociated multipotent epidermal cells can be derived from human fetal scalp, adult scalp, human newborn foreskin, and other sources. While not fetal, foreskin cells may still be early enough to proliferate better than adult cells. Certain examples of epidermal cells can contain a range of 20-90 percent multipotent cells. Dissociated cells may have been separated from other cells in a tissue. This serparation may have been carried out by digestion with an enzyme to break apart the extracellular matrix securing the cells to form the tissue.

Dissociated multipotent dermal cells can be derived from human fetal scalp, adult scalp, human neonatal foreskin, and other sources. Neonatal cells can be multipotent, undifferentiated, and partially differentiated cells that are derived from newborn infants, such as from foreskins. Additional sources of epidermal cells can include truncal skin, oral mucosa, and mesenchymal stem cells undergoing a mesenchymal to epithelial transition. Other sources of multipotent cells, including SOX2 positive mesenchymal cells, can be derived from any tissues including bone marrow or blood derived cells, and melanocytes, adipocytes, neural or endothelial precursors. These cells can also be generated from an induced pluripotent stem cell (iPSC) source.

In block 320, the sourced cells may be isolated from their source tissue. An isolated cell may be in an environment different from that in which the cell naturally occurs. For example, dermal cells may be separated from a hair follicle. Epidermal and dermal cells may be isolated from human skin tissue by first cutting the skin into small strips. For example, the strips may be approximately five-by-five millimeters in size.

According to certain examples, the strips may be incubated in a phosphate buffered saline solution (PBS) of dispase. Dispase is a protease operable to cleave fibronectin and collagen. The incubation can be carried out at approximately four degrees Celsius overnight. After incubation, epidermis and dermis may be separated, for example using forceps.

For dermal cell preparations, the dermis may be minced using crossed scalpel blades. The tissue may then be incubated in collagenase. After approximately thirty minutes, the dermal solution may be neutralized and passed through a filter. The filtrate may then be centrifuged and rinsed with PBS for plating. Adult dermal cells may be isolated from full-thickness, adult scalp skin by a similar method where the epidermis may remain in the preparation.

For epidermal cell isolation, cells may be collected from the isolated fetal or neonatal epidermis. After incubation in trypsin, the tissue may be neutralized, centrifuged, and rinsed with PBS before plating. Epidermal cells may be isolated from neonatal human foreskins in a similar fashion.

In block 330, the isolated cells may be cultured. An example cell culturing method is presented in further detail with respect to FIG. 4.

In block 340, cultured cells may be applied to a substrate. Cultured dermal and epidermal cells may have been co-cultured and may be suspended into a slurry. According to certain embodiments, other cell types, such as melanocytes for pigmentation or endothelial cells for vascular formation, may be add into the cell slurry. The cell slurry may be transferred onto an inert, biocompatible substrate. The substrate can be preferably easily removed from the cells once the human skin is reconstituted. Various biodegradable materials can be used as the substrate such as polyesters like polylactic acid and polyglycolic acid, and proteins like collagen, gelatin, fibrin, and albumin. Other exemplary non-biodegradable substrate materials can include carbon, silicon, or polytetrafluoroethylene. Additional example substrates may include silicon membranes, polyethylene terephthalate (PET) membranes, or BD Falcon cell culture inserts.

Bioactive substrates such as SIS and amnion derived membranes could also be used to enhance the formation of skin. Substrates with incorporated growth factors and signaling molecules (i.e. FGF, BMP, SHH) could also be utilized.

The cell suspension can be applied to the substrate and then incubated at 37 degrees Celsius an hour or two. The incubation may be carried out in a cell culture incubator, allowing the cells to adhere to form a cohesive mass of cells. Cohesive cells may display the ability to connect to each other and form a conglomerate. The substrate may be stored at four degrees Celsius for eight to ten hours prior to exposure.

In block 350, the prepared cells and substrate may be applied to the recipient. Topical immunosuppressant may be delivered before or after placing the cells to enhance survival and proliferation of the grafted cells. The immunosuppressant may be applied by superficial injection, microneedles, topically, or by any combination thereof. A topical immunosuppressant may enhance the formation of the human skin, but is generally not strictly necessary. Example immunosuppressant may include TGF beta 1, TGF beta 2, ACTH, alpha MSH, Cyclosporine A, or Rapamycin. These immunosuppressant can be applied to the graft to decrease inflammation and reduce the likelihood for rejection of the graft. Administration of immunosuppressant may be particularly preferred when melanocytes are also administered.

Generally the substrate is secured with tape, staples or sutured. Sterile dressings can be applied to reduce infection. The substrate with dermal and epidermal cells adhered thereto may be placed onto the musculature fascial plane within the skin wound. The substrate may be placed with the cells contacting the wound and with the substrate on top. The cells may begin to form skin including skin appendages once the cells are applied to the wound. It is believed that the combination of cells when present in the wound are able to reorient and generate cues that promote the proper formation of complex components of human skin including hair follicles and associated glands.

In block 360, reconstitution of a full-thickness, functional skin organ 110 may be supported. Reconstitution can replicate the original developmental process. The grafted cells can interact with each other and with other cells and produce a functioning, full-thickness skin organ 110. As demonstrated by the mouse graft example, the reconstituted human skin organ 110 can contain cycling mature human hair follicles 160, which produce normal pigmented hair shafts. The reconstituted human skin organ 110, even when grown on another animal, can contain human epidermis 120, dermis 130, nerves 150, blood vessels 190, sweat glands 180, sebaceous glands 170, a full subcutis layer 140, and the hair follicles 160. The reconstituted skin organ 110 can remain human in its morphology and behavior. The reconstituted skin organ 110 may be better vascularized and more long-lived than transplanted skin xenografts from tissues belonging to individuals of different species. The reconstituted human skin organ 110 can contain human stem cell niches and thus may be able to heal after injury and cycle hair follicles.

Reconstitution of a full-thickness, functional skin organ 110 can involve growth of new hair follicles 160. Generally, cultures of high SOX2 expressed dermal cells can induce formation of more hair follicles 160. In one example, the reconstituted skin organ 110 may cover an area of up to two square centimeters and support from 50-2000 mature hair follicles 160 per square centimeter.

The events of hair-follicle morphogenesis can be summarized as formation of an epidermal platform, followed by dermal condensations, followed by epithelial invagination to form the follicular wall, followed by formation of dermal papillae (DP) at the base of the hair follicle 160, followed by molecular differentiation of hair-shaft components, followed by the ability to grow and cycle while preserving stem cells and DP for the next cycle, and finally the ability to regenerate. The human skin organ 110 cultured human cells that is described herein may progress through these steps as it forms on the graft recipient. The hair follicles 160 that are formed are able to cycle just as hair follicles usually do. This demonstrates the generated cells' ability to regenerate.

In block 370, clinical therapies, for humans and other animals, may be supported through the generation of a full-thickness human skin organ 110 from culture-expanded human cells. The skin organ 110 generation method may combine a cultured dermal cell and a culture epidermal cell. The skin organ 110 generation method may leverage cells derived from adult human scalp tissue, foreskin tissues, neonatal tissues, and/or fetal tissues. The skin organ 110 generation method may leverage SOX2 positive cells from any tissue source. The skin organ 110 generation method may leverage epidermal cells from one or more tissue sources having high colony forming capacity. The skin organ 110 generation method may comprise freezing and thawing cells. The skin organ 110 generation method may comprise increasing the potency of cells using a low oxygen environment. The skin organ 110 generation method may comprise cell aggregation to increase the potency of the cell types. The skin organ 110 generation method may isolate, culture, freeze and thaw cells having capabilities to generate complete human skin and variations of complete human skin. The skin organ 110 generation method may reprogram adult dermal fibroblasts into fetal-like dermal papilla cells. The skin organ 110 generation method may use cells for the development of iPSC strains, and differentiate iPSCs into dermal papilla cells. The skin organ 110 generation method may comprise using an inert membrane in combination with cells, using a biological membrane in combination with cells, or using a biologically active membrane in combination with cells. The skin organ 110 generation method may be applied to wound healing. The skin organ 110 generation method may be applied for treatment of scar tissue to produce skin with nerves, functional sweat glands, subcutis, and philosebaceous units. The skin organ 110 generation method may be applied for treatment of scar tissue to produce skin with functional sweat glands, subcutis, and philosebaceous units. The skin organ 110 generation method may be applied for treatment of scar tissue to produce skin with functional sweat gland and subcutis. The skin organ 110 generation method may be applied for treatment of scar tissue to produce skin with a sub cutis. The skin organ 110 generation method may be applied to treating vitiligo. The skin organ 110 generation method may be applied to treatments for burns, chronic wounds, diabetic ulcers, skin aging, wrinkles, eczema, psoriasis, scar tissue, and/or nerve damage. The skin organ 110 generation method may be applied to generate philosebaceous units. The skin organ 110 generation method may be applied to accelerate wound healing, amputation wound closure, scar removal, and/or tattoo removal. The skin organ 110 generation method may be applied to reconstructive surgery for ears, noses, eyelids, or any other anatomical structures. The skin organ 110 generation method may be applied to reducing, or preventing, scarring from wounds or surgeries.

In block 380, human skin models may be provided for the study of human skin and its appendages. These studies may include skin diseases, wound healing, drug delivery, and developmental biology. Furthermore, skin is an excellent model to study the basic biology of organ regeneration and translational approaches to regenerative medicine. Generation of a complete human skill organ 110 on a mouse, other laboratory animal, or other system may be used for bioequivalence drug testing, as a model for drug delivery, as a model for investigation of ultraviolet damage and phototoxicity, or as a model for studying skin drugs. Generation of a complete human skill organ 110 may be used as a model for studying hair follicle drugs, a model for studying sweat gland drugs, a model for studying sebaceous gland drugs, a model for studying skin aging treatments, a model for studying adipose reduction drugs, a model for studying varicose veins, or as a model for studying corrosive skin tests. Generation of a complete human skill organ 110 may be used as a model for studying skin treatment technologies such as lasers, cryotherapy, derma abrasion, or for development of personalized medicine treatment options. Generation of a complete human skill organ 110 may be used for screening new drugs for effectiveness and/or safety. Generation of a complete human skill organ 110 may be used as a model for studying skin injury. Generation of a complete human skill organ 110 may be used as a model for studying burn wound treatment. Generation of a complete human skill organ 110 may be used as a model for studying chronic wounds associated with diabetic ulcers. Generation of a complete human skill organ 110 may be used as a model for studying skin disease development and or treatment such as those associated with psoriasis, skin cancer, eczema, alopecia areata, androgenic alopecia, epidermal bubalosa, acne, lupus, or skin aging.

Figure 4:
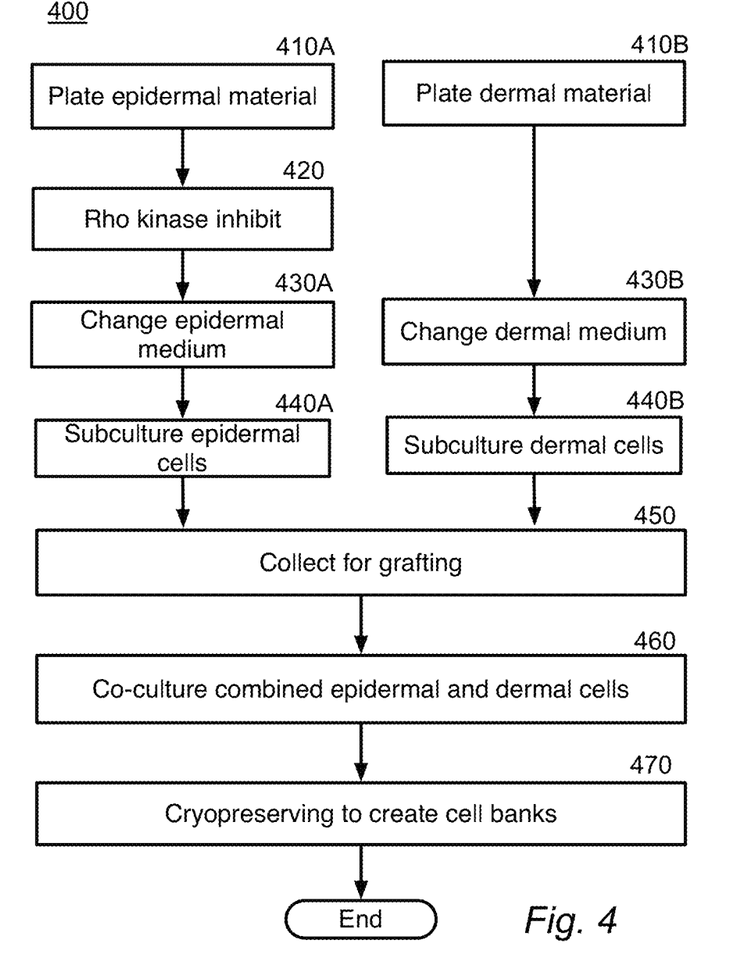
FIG. 4 is a block flow diagram depicting a method for culturing cells in accordance with one or more embodiments presented herein.

FIG. 4 is a block flow diagram depicting a method 400 for culturing cells in accordance with one or more embodiments presented herein.

In block 410A, epidermal material may be plated. The plating may be carried out in a matrix-precoated flask. An example medium for epidermal cell culturing can include a progenitor cell targeted liquid culture medium including both basal medium and separate supplements such as CnT-07. Such a basal medium may contain amino acids, minerals, vitamins, and organic compounds. Such a basal medium may be free of proteins.

In block 410B, dermal material may be plated. An example medium for dermal cell culturing can include a three-to-one ratio of Dulbecco's Modified Eagle Medium and Nutrient Mixture F-12 (DMEM/F-12). The medium may also include approximately five percent fetal bovine serum (FBS) or fetal calf serum. The DMEM/F-12 medium may contain 0.1% penicillin/streptomycin, 40 µg/ml fungizone, 40 ng/ml FGF2, 20 ng/ml EGF, and 2% B27 supplement.

With respect to both block 410A and block 410B, culture conditions may be held close to physiological conditions. The pH of the culture media may be close to physiological pH, preferably between pH 6-8, more preferably close to pH 7, and even more particularly about pH 7.4. Cells may be cultured at a temperature close to physiological temperature, preferably between 30° C.-40° C., more preferably between 32° C.-38° C., and most preferably between 35° C.-37° C. Oxygen concentrations can range from two to twenty percent oxygen, or more preferably two to ten percent oxygen. Low oxygen cultures can enhance skin cell trichogenicity and can increase SOX2 expression.

In block 420, epidermal cells may be rho kinase (ROCK) inhibited by exposure to a ROCK inhibitor. Rho kinase is a serine-threonine kinase that mediates various important cellular functions such as cell shape, by acting on the cytoskeleton. The addition of ROCK inhibitors to a cell culture medium can block apoptosis, thereby allowing for the selection of a specific population of cells that otherwise may not survive. An example ROCK inhibitor can include Y-27632. According to certain examples, the cells may be cultured with a ROCK inhibitor for three days. After three days of culture, the ROCK inhibitor may be removed from the culture.

In blocks 430A and 430B, the culture mediums may be changed. According to one specific example, changing of the epidermal medium (as in block 430A) may be carried out every other day, or approximately every other day. According to one specific example, changing of the dermal medium (as in block 430B) may be carried out every five days, or approximately every five days.

In blocks 440A and 440B, the cells may be subcultured or passaged. For each passage, the cells may be sub-cultured or split and grown under cultured conditions for extended periods of time to increase the number of cells. Each cycle where the cells are transferred from one vessel to another may be considered a passage cycle. According to one specific example, subculturing of the epidermal cells (as in block 440A) may be performed when the cell density attains 80-90% confluence, and the passage dilution is one-to-three. According to one specific example, subculturing of the dermal cells (as in block 440B) may be performed when the cell density attains 80-90% confluence, and the passage dilution is one-to-five.

In block 450, both dermal and epidermal cells may be collected for grafting. Collection may occur after cell density has reached 90-100% confluence. Collection for grafting may occur after one to four culturing passages.

In block 460, both dermal and epidermal cells may be combined to continue in a single combined culture. This may be referred to as co-culturing where the dermal cells and epidermal cells are allowed to interact together in a single combined culture. According to one example, the dermal and epidermal cells are propagated separately up to the third passage for up to three weeks to increase the number of cells prior to being combined into a single co-culture. Combining of epidermal cells with dermal cells may be performed at different ratios of one-to-one through one-to-ten. The combined culture may be carried out in a low adhesive plate, such as a six-well low adhesive plate. The expanded dermal and epidermal cells may be combined to produce a cell slurry. According to certain examples, the slurry may be suspended in a cell culture medium.

In block 470, cells being cultured may be cryopreserved. Cryopreservation may occur after one or two passages. Cryopreservation may be used to establish cell banks to be thawed in the future for use in techniques presented herein.

The example systems, methods, and acts described in the embodiments presented previously are illustrative, and, in alternative embodiments, certain acts can be performed in a different order, in parallel with one another, omitted entirely, and/or combined between different example embodiments, and/or certain additional acts can be performed, without departing from the scope and spirit of embodiments of the invention. Accordingly, such alternative embodiments are included in the inventions described herein.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of the invention defined in the following claims, the scope of which is to be accorded the broadest interpretation so as to encompass such modifications and equivalent structures.

What is claimed:

1. A method for skin organ generation comprising:
   isolating epidermal and dermal cells from human tissues;
   culturing the isolated epidermal cells;
   culturing the isolated dermal cells;
   combining the cultured epidermal cells and the cultured dermal cells;
   co-culturing the combined epidermal cells and dermal cells in the presence of less than ten percent oxygen;
   implanting the co-cultured cells onto a recipient organism; and
   supporting generation of a full-thickness skin organ from the implanted cells.

2. The method of claim 1, further comprising the step of applying the co-cultured cells to a substrate, and wherein implanting comprises attaching the substrate to the organism.

3. The method of claim 1, wherein isolating cells from human tissues comprises isolating adult or fetal hair follicle cells.

4. The method of claim 1, wherein isolating cells from human tissues comprises isolating neonatal foreskin cells.

5. The method of claim 1, wherein culturing the isolated epidermal cells comprises exposing the cells to a rho kinase inhibitor.

6. The method of claim 1, wherein the skin organ comprises fully cycling hair follicles.

7. The method of claim 1, wherein isolating cells from human tissues comprises isolating highly trichogenic, SOX2 positive cell populations.

8. The method of claim 1, wherein the generated skin organ supports wound healing.

9. The method of claim 1, wherein the organism is a non-human laboratory animal and the generated skin organ supports a human skin model for testing or experimentation.

10. The method of claim 1, wherein the skin organ comprises sweat glands, nerves, and subcutis.

11. A method for skin organ generation comprising:
    isolating epidermal and dermal cells from human tissue;
    culturing the isolated epidermal cells, wherein culturing the isolated epidermal cells comprises exposing the cells to a rho kinase inhibitor;
    culturing the isolated dermal cells;
    combining the cultured epidermal cells and the cultured dermal cells;
    co-culturing the combined epidermal cells and dermal cells in the presence of less than ten percent oxygen to enrich SOX2 expression;
    implanting the co-cultured cells onto a recipient organism; and
    supporting generation of a full-thickness skin organ from the implanted cells, wherein the skin organ comprises fully cycling hair follicles.

12. The method of claim 11, wherein isolating cells from human tissues comprises isolating neonatal foreskin cells.

13. The method of claim 11, wherein isolating cells from human tissues comprises isolating highly trichogenic cell populations.

14. The method of claim 11, wherein the skin organ comprises sweat glands, nerves, and subcutis.

15. The method of claim 11, wherein the generated skin organ supports wound healing.

16. The method of claim 11, wherein the generated skin organ supports hair regeneration.

17. The method of claim 11, further comprising the step of applying the co-cultured cells to a substrate, and wherein implanting comprises attaching the substrate to the organism.

18. The method of claim 11, further comprising the steps of suspending the co-cultured cells into a slurry and applying the slurry to a substrate prior to implanting.

19. The method of claim 11, wherein the organism is a non-human laboratory animal and the generated skin organ supports a human skin model for testing or experimentation.

20. A method for skin therapy comprising:
    isolating dermal cells from human tissue;
    isolating epidermal cells from human tissue;
    co-culturing the isolated epidermal cells and the isolated dermal cells in the presence of less than ten percent oxygen;

implanting the co-cultured cells onto a recipient organism; and supporting generation of a full-thickness skin organ from the implanted cells, wherein the skin organ comprises functioning epidermis, dermis, and hypodermis layers.

* * * * *